Figure 1:
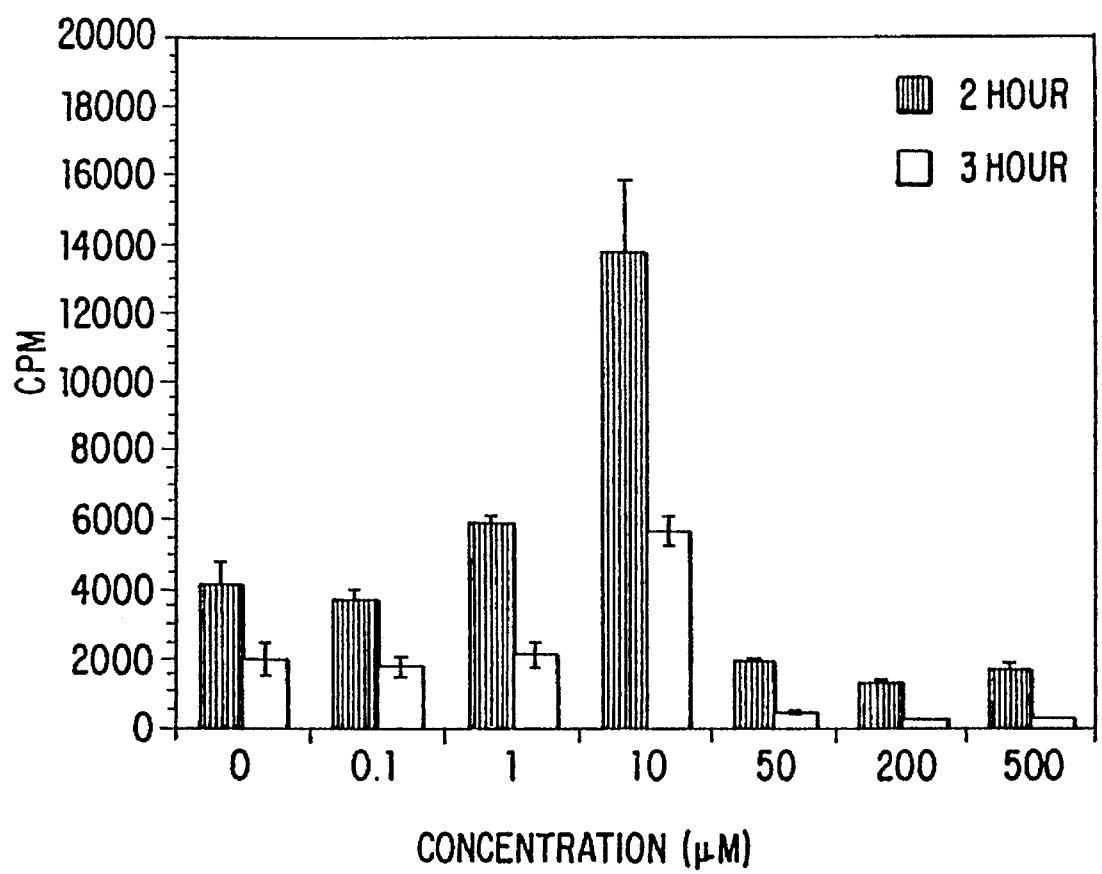

United States Patent [19]
Tang et al.

[11] Patent Number: 5,602,171
[45] Date of Patent: Feb. 11, 1997

[54] METHODS OF INHIBITING PHOSPHATASE ACTIVITY AND TREATMENT OF DISORDERS ASSOCIATED THEREWITH USING NAPHTHOPYRONES AND DERIVATIVES THEREOF

[75] Inventors: Peng C. Tang, Moraga; Gerald McMahon, Kenwood, both of Calif.

[73] Assignee: Sugen Inc., Redwood City, Calif.

[21] Appl. No.: 481,955

[22] Filed: Jun. 7, 1995

[51] Int. Cl.$^6$ .......................... A61K 31/35; C07D 309/32
[52] U.S. Cl. ............................................. 514/455; 549/389
[58] Field of Search ............................. 514/455; 549/389

[56] References Cited

U.S. PATENT DOCUMENTS 5,155,031  10/1992  Posner et al. ............................ 435/184

OTHER PUBLICATIONS

Taniguchi, 1995, "Cytokine Signaling Through Nonreceptor Protein Tyrosine Kinases", Science 268:251–255.
Pawson, 1995, "Protein Modules and Signalling Networks", Nature 373:573–580.
Cohen et al., 1995, "Modular Binding Domains in Signal Transduction Proteins", Cell 80:237–248.
Heldin, 1995, "Dimerization of Cell Surface Receptors in Signal Transduction", Cell 80:213–223.
Xiao et al., 1994, "Syp (SH–PTP2) is a Positive Mediator of growth Factor–stimulated Minogenic Signal Trtansduction", J Biol Chem 269:21244–21248.
Schlessinger et al., 1994, "SH2/SH3 Signalling Proteins", Curr Opin Genet Dev 4:25–30.
Darnell et al., 1994, "Jak–STAT Pathways and Transcriptional Activation in Responce to IFNs and Other Extracellular Signalling Proteins", Science 264:1415–1421.
Millauer et al., 1994 "Globlastoma Growth Inhibited In Vivo By a Dominant–Negative Flk–1 Mutant", Nature 367:576–579.
Mauro and Dixon, 1994, "Zip Codes 'Direct Intracellular Protein Tyrosine Phosphatases to the Correct Cellular 'Address'", Trends Biochem sci 19:151–155.
Burke et al., 1994, "Potent Inhibition of Insulin Receptor Dephosphorylation By a Hexamer Peptide Containing the Phosphotyrosyl Mimetic F$_2$Pmp", Biochem Biophys Res Comm 204:129–134.
den Hertog et al., 1993, "Receptor Protein Tyrosine Phosphatase α Activates pp620$^{c-src}$ and is Involved in Neuronal Differentiation", EMBO J 12:3789–3798.
Schultz et al., 1993, "Mutations at the Murine Motheaten Locus Are Withiin Locus Are Within the Hematopoietic Cell Protein–Tyrosine Phosphatase (Hcph) Gene", Cell 73:1445–1454.
Jiang et al., 1993, "Cloning and Characterization of R–PTP–k, a New Member of the Receptor Protein Tyrosine Phosphatase Family with a Proteolytically Cleaved Adhesion Molecule–Like Extracellular Region", Moll Cell Biol 13:2942–2951.

Vogel et al., 1993, "Activation of a Phosphotyrosine Phosphatase by Tyrosine Phosphorylation", Science 259:1611–1614.
Sadowski et al., 1993, "A Common Nuclear Signal Transuction Pathway Activated By Growth Factor and Cytokine Receptors", Science 261:1739–1744.
Yan et al., 1993 "A Novel Receptor Tyrosine Phosphatase–α That is Highly Expressed in the Nervous System", J Biol Chem 268:24880–24886.
Goldstein, 1992 "Protein–Tyrosine Phosphatases and the Regulation of Insulin Action", J Cell Biochem 48:33–42.
Hegde et al., 1992, "SCH 45752—An Inhibitor of Calmodulin–Sensitive Cyclic Nucleotide Phosphodiesterase Activity", J Antibiotics 48:207–213.
Pot and Dixon, 1992, "A Thousand and Two Protein Tyrosine Phosphatases", Biochem Biophys Acta 1136:35–43.
Spivak et al., 1992, "Protein Kinases and Phosphatases Are Involved in Erythropoletin–mediated Signal Transduction", Exp Hermatol 20:500–504.
Saito and Streuli, 1991, "Molecular Characterization of Protein Tyrosine Phosphatases", Cell Growth Differ 2:59–65.
Fischer et al., 1991, "Protein Tyrosine Phosphatases: A Diverse Family of Intracellular and Transmembrane Enzymes", Science 352:401–406.
Shen et al., 1991, "A Protein–Tyrosine Phosphatase With Sequence Similarity to the SH2 Domain of the Protein–Tyrosine Kinases", Nature 352:736–739.
Kaplan et al., 1990, "Cloning of Three Human Tyrosine Phosphatases Reveals a Multigene Family of Receptor–linked Protein–Tyrosine–Phosphatases Expressed in Brain", Proc Natl Acad Sci 87:7000–7004.
Lund et al., 1990, "Prevention of Insulin–Dependent Diabetes Mellitus in Non–Obese Diabetic Mice by Transgenes Encoding Modified I–A β–Chain or Normal I–E α–Chain", Nature 345:727–729.
Cool et al., 1989, "cDNA Isolated From a Human T–Cell Library Encodes a Member of the Protein–Tyrosine–Phosphatase Family", Proc Natl Acad Sci 86:5257–5261.
Solomon et al., 1989, "Studies of Insulin Resistance in the Streptozocin Diabetic and BB Rat: Activation of Low Km cAMP Phosphodiesterace by Insulin", Am J Med Sci 297:372–376.
Charbonneau et al., 1989, "Human Placenta Protein–Tyrosine–Phosphatase Amino Acid Sequence and Relationship to a Family of Receptor–like Proteins", Proc. Natl Acad Sci 86:5252–5256.

(List continued on next page.)

*Primary Examiner*—Johann Richter
*Assistant Examiner*—Laura R. Cross
*Attorney, Agent, or Firm*—Pennie & Edmonds

[57] ABSTRACT

The present invention relates to organic molecules capable of inhibiting protein tyrosine phosphatase activity. The invention further relates to the use of such molecules to modulate or regulate signal transduction by inhibiting protein tyrosine phosphatase activity. Finally, the invention relates to the use of such molecules to treat various disease states including diabetes mellitus.

12 Claims, 1 Drawing Sheet

OTHER PUBLICATIONS

Charbonneau et al., 1988, "The Leukocyte Antigen (CD45) A Positive Receptor–linked Protein Tyrosine Phosphatase", Proc. Nat Acad Sci 85:7182–7186.

Suganuma et al., 1988, "Okadaic Acid: An Additional Non–Phorbol–12–Teterdecanoate–13–acetate–type Tumor Promoter", Proc Natl Acad Sci 85:1768–1771.

Slamon et al., 1987, "Human Breast Cancer: Correlation of Relapse and Survival with Amplification of the HER–2 ineu Oncogene", Science 235:177–182.

Dubyak and Kleinzeller, 1980, "The Insulin–mimetic Effects of Vanadate in Isolated Rat Adipocytes", J Biol Chem 255:5306–5312

Shechter and Karlish, 1980, "Insulin–like Stimulation of Glucose Oxidation in Rat Adipocytes by Vanadyl (IV) Ions", Nature 284:556–558.

METHODS OF INHIBITING PHOSPHATASE ACTIVITY AND TREATMENT OF DISORDERS ASSOCIATED THEREWITH USING NAPHTHOPYRONES AND DERIVATIVES THEREOF

1. INTRODUCTION

The present invention relates to compounds capable of modulating and/or regulating the activity of phosphotyrosine phosphatases that regulate signal transduction. Specifically, the present invention relates to the use of such compounds for the treatment of diseases caused by dysfunctional signal transduction.

2. BACKGROUND OF THE INVENTION

2.1. Signal Transduction

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of tyrosine residues on proteins. The phosphorylation state of a protein may affect its conformation and/or enzymic activity as well as its cellular location. The phosphorylation state of a protein is modified through the reciprocal actions of protein tyrosine kinases (PTKs) and protein tyrosine phosphatases (PTPs) at various specific tyrosine residues.

2.2. Protein Tyrosine Kinases and Phosphatases

A common mechanism by which receptors regulate cell function is through an inducible tyrosine kinase activity which is either endogenous to the receptor or is imparted by other proteins that become associated with the receptor. (Darnell et al., 1994, Science 264:1415–1421; Heldin, 1995, Cell 80:213–223; Pawson, 1995, Nature 373:573–580).

Protein tyrosine kinases comprise a large family of transmembrane receptor and intracellular enzymes with multiple functional domains (Taylor et al., 1992 Ann. Rev. Cell Biol. 8:429–62). The binding of ligand allosterically transduces a signal across the cell membrane where the cytoplasmic portion of the PTKs initiates a cascade of molecular interactions that disseminate the signal throughout the cell and into the nucleus. Many receptor protein tyrosine kinase (RPTKs), such as epidermal growth factor receptor (EGFR) and platelet-derived growth factor receptor (PDGFR) undergo oligomerization upon ligand binding, and the receptors self-phosphorylate (via autophosphorylation or transphosphorylation) on specific tyrosine residues in the cytoplasmic portions of the receptor (Schlessinger and Ullrich, 1992, Neuron, 9:383–91, Heldin, 1995, Cell 80:213–223). Cytoplasmic protein tyrosine kinases (CPTKs), such as Janus kinases (e.g., JAK1, JAK2, TYK2), Src kinases (e.g., src, lck, fyn) are associated with receptors for cytokines (e.g., IL-2, IL-3, IL-6, erythropoietin) and interferons, and antigen receptors. These receptors also undergo oligomerization, and have tyrosine residues that become phosphorylated during activation, but the receptor polypeptides themselves do not possess kinase activity.

Like the PTKs, the protein tyrosine phosphatases (PTPs) comprise a family of transmembrane and cytoplasmic enzymes, possessing at least an approximately 230 amino acid catalytic domain containing a highly conserved active site with the consensus motif [I/V]HCXAGXXR[S/T]G. The substrates of PTPs may be PTKs which possess phosphotyrosine residues or the substrates of PTKs. (Hunter, 1989, Cell 58:1013–16; Fischer et al., 1991, Science 253:401–6; Saito & Streuli, 1991, Cell Growth and Differentiation 2:59–65; Pot and Dixon, 1992, Biochem. Biophys. Acta, 1136:35–43).

Transmembrane or receptor-like PTPs (RPTPs) possess an extracellular domain, a single transmembrane domain, and one or two catalytic domains followed by a short cytoplasmic tail. The extracellular domains of these RPTPs are highly divergent, with small glycosylated segments (e.g., RPTPα, RPTPε), tandem repeats of immunoglobulin-like and/or fibronectin type III domains (e.g., LAR) or carbonic anhydrase like domains (e.g., RPTPγ, RPTPβ). These extracellular features might suggest that these RPTPs function as a receptor on the cell surface, and their enzymatic activity might be modulated by ligands. Intracellular or cytoplasmic PTPs (CPTPs), such as PTP1C, PTP1D, typically contain a single catalytic domain flanked by several types of modular conserved domains. For example, PTP1C, a hemopoietic cell CPTP is characterized by two Src-homology 2 (SH2) domains that recognize short peptide motifs bearing phosphotyrosine (pTyr).

In general, these modular conserved domains influence the intracellular localization of the protein. SH2-containing proteins are able to bind pTyr sites in activated receptors and cytoplasmic phosphoproteins. Another conserved domain known as SH3 binds to proteins with proline-rich regions. A third type known as pleckstrin-homology (PH) domain has also been identified. These modular domains have been found in both CPTKs and CPTPs as well as in non-catalytic adapter molecules, such as Grbs (Growth factor Receptor Bound), which mediate protein-protein interactions between components of the signal transduction pathway (Skolnik et al., 1991, Cell 65:83–90; Pawson, 1995, Nature 373:573–580).

Multiprotein signaling complexes comprising receptor subunits, kinases, phosphatases and adapter molecules are assembled in subcellular compartments through the specific and dynamic interactions between these domains with their binding motifs. Such signaling complexes integrate the extracellular signal from the ligand-bound receptor and relay the signal to other downstream signaling proteins or complexes in other locations inside the cell or in the nucleus (Koch et al., 1991, Science 252:668–674; Pawson, 1994, Nature 373:573–580; Mauro et al., 1994, Trends Biochem Sci 19:151–155; Cohen et al., 1995, Cell 80:237–248).

2.3. Abnormal Signal Transduction in Human Diseases

The levels of tyrosine phosphorylation required for normal cell growth and differentiation at any time are achieved through the coordinated action of PTKs and PTPs. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus which is characterized by insufficient or a lack of insulin signal transduction can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235:77–82) and that antibodies capable of blocking the activity of this enzyme can abrogate tumor growth (Drebin et al., 1988, Oncogene 2:387–394). Blocking the signal transduction capability of tyrosine kinases such as Flk-1 and the PDGF receptor have been shown to block tumor growth in animal models (Millauer et al., 1994, Nature 367:577; Ueno et al., Science, 252:844–848).

Relatively less is known with respect to the direct role of tyrosine phosphatases in signal transduction; PTPs may play a role in human diseases. For example, ectopic expression of RPTPα produces a transformed phenotype in embryonic fibroblasts (Zheng et al., Nature 359:336–339), and overexpression of RPTPα in embryonal carcinoma cells causes the cells to differentiate into a cell type with neuronal phenotype (den Hertog et al., EMBO J 12:3789–3798). The gene for human RPTPγ has been localized to chromosome 3p21 which is a segment frequently altered in renal and small lung carcinoma. Mutations may occur in the extracellular segment of RPTPγ which renders a RPTP that no longer respond to external signals (LaForgia et al., Wary et al., 1993, Cancer Res 52:478–482). Mutations in the gene encoding PTP1C (also known as HCP, SHP) are the cause of the motheaten phenotype in mice which suffer severe immunodeficiency, and systemic autoimmune disease accompanied by hyperproliferation of macrophages (Schultz et al., 1993, Cell 73:1445–1454). PTP1D (also known as Syp or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, J Biol Chem 269:21244–21248).

It has been reported that some of the biological effects of insulin can be mimicked by vanadium salts such as vanadates and pervanadates. Vanadates and pervanadates are known to be non-specific phosphatase inhibitors. However, this class of compounds is toxic because each compound contains a heavy metal (U.S. Pat. No. 5,155,031; Fantus et al., 1989, Biochem., 28:8864–71; Swarup et al., 1982, Biochem. Biophys. Res. Commun. 107:1104–9).

3. SUMMARY OF THE INVENTION

The present invention is directed to the use of organic molecules capable of modulating and/or regulating signal transduction by inhibiting the activity of protein tyrosine phosphatases (PTPs). The invention therefore encompasses methods of inhibiting protein tyrosine phosphatase activity by contacting cells with an effective amount of a compound of the present invention or a pharmaceutically acceptable salt thereof. Further, the invention encompasses methods of treating disease states in mammals, including humans, which are ameliorated by modulating and/or regulating signal transduction through the inhibition of protein tyrosine phosphatase activity. Such disease states or disorders include but are not limited to diabetes and cancer.

3.1. Definitions

By the term "alkyl" as used herein is meant a straight or branched chain saturated hydrocarbon group having from 1 to 20 carbons such as methyl, ethyl, isopropyl, n-butyl, s-butyl, t-butyl, n-amyl, isoamyl, n-hexyl, n-octyl and n-decyl. The terms "alkenyl" and "alkynyl" are used to mean straight or branched chain hydrocarbon groups having from 2 to 10 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl. The term "phenylalkyl" means the aforementioned alkyl groups substituted by a phenyl group such as benzyl, phenethyl, phenopropyl, 1-benzylethyl, phenobutyl and 2-benzylpropyl. The term "aryl" as used herein is meant to include a monocyclic or bicyclic rings, wherein at least one ring is aromatic including aromatic hydrocarbons or hetero-aromatic hydrocarbons. The term "hydroxy-alkyl" means the aforementioned alkyl groups substituted by a single hydroxyl group such as 2-hydroxyethyl, 2-hydroxypropyl, 3-hydroxypropyl, 4-hydroxybutyl, 1-hydroxybutyl and 6-hydroxyhexyl. The terms "alkylthio, alkenylthio, alkynylthio, alkylthio, hydroxyalkylthio and phenyl-alkylthio" as used herein mean the aforementioned alkyl, alkenyl, alkynyl, hydroxy-alkyl and phenyl-alkyl groups linked through a sulfur atom to group R.

The term "substituted" as used herein means that the group in question, e.g., alkyl group, aryl group, etc., may bear one or more substituents including but not limited to halogen, hydroxy, cyano, amino, nitro, mercapto, carboxy and other substituents known to those skilled in the art.

The terms "saturated" as used herein means an organic compound with neither double or triple bonds. The term "unsaturated" as used herein means an organic compound containing either double or triple bonds.

4. BRIEF DESCRIPTION OF THE DRAWINGS

FIG. 1. Dose response effect of compound 1 on the uptake of 2-deoxy-$^3$H-glucose in 3T3-L1 cells, a preadipocyte cell line.

5. DETAILED DESCRIPTION OF THE INVENTION

The present invention is directed to the use of compounds capable of inhibiting the activity of protein tyrosine phosphatases (PTPs) for modulating or triggering signal transduction. The invention is further directed to the regulation of cellular processes that are controlled by signal transduction through the inhibition of the activity of PTPs by the compounds. The invention further provides for the use of such compounds in the treatment of a subject having a disorder caused by dysfunctional signal transduction.

In one embodiment of the invention, the compounds of the invention are capable of inhibiting the activity of protein tyrosine phosphatases, that are transmembrane or intracellular, and that may have one or more characteristic catalytic domains. The amino acid sequences of the PTPs in the catalytic domains may include but are not limited to [I/V] HCXAGXXR[S/T]G (single-letter amino acid code; X is any amino acid). In addition, the PTPs may possess one or more modular conserved domains, which include but are not limited to, SH2, SH3 and PH domains. In a specific embodiment of the invention, the compounds of the invention can be used to inhibit the phosphatase activity of PTP1B (Charbonneau et al., 1989, Proc. Natl Acad Sci USA, 86: 5252–5256), T-cell PTP (Cool et al., 1989, Proc Natl Acad Sci USA, 86: 5257–5261, PTP1C (Shen et al., 1991, Nature, 352: 736–739), PTP1D (Vogel et al., 1993, Science 259: 1611–1614), RPTPα, RPTPβ, RPTPγ (Kaplan et al., 1990, Proc Natl Acad Sci USA, 87: 7000–7004), RPTPσ (Yan et al., 1993, J Biol Chem 268: 24880–24886), RPTPκ (Jiang et al., 1993, Mol Cell Biol, 13: 2942–2951) and CD45 (Charbonneau et al., 1988, Proc Natl Acad Sci USA 85: 7182–7186). The PTPs preferred in the invention are of human origin. Inhibition of phosphatase activity that is substantially specific to a PTP or a set of PTPs in a signaling pathway is preferred.

The term "signal transduction" as used herein is not limited to transmembrane signaling, and includes the multiple pathways that branch off throughout the cell and into the nucleus. Such signaling pathways may include but are not limited to the Ras pathway (Schlessinger, 1994, Curr Opin Genet Dev 4:25–30), the JAK/STAT pathways (Sadowski et al., 1994, Science 261:1739–1744), the phosphoinositide 3-kinase pathway and the phospholipase C-γ pathway. As used herein, the term "modulation" or "modulating" shall mean upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival; as well as abnormal processes, such as transformation, blocking of differentiation and metastasis.

A signal may be triggered by the binding of a ligand to its receptor on the cell surface, and the signal is transduced and propagated by the phosphorylation or dephosphorylation of specific tyrosine residues on various substrates inside the cell. The specific interactions between the PTKs, PTPs and their substrates may involve the formation of a transient or stable multimolecular complex on the inner face of the plasma membrane or in other subcellular compartments including the nucleus. A substrate may contain one or more tyrosine residues that are phosphorylated or dephosphorylated by PTKs or PTPs in the signaling pathway. Such substrates may include the receptor and its subunits, molecules associated with or recruited to the receptor such as cytoplasmic kinases, cytoplasmic phosphatases, adapter molecules, cytoskeletal proteins and transcription factors. The term receptor as used herein may include, but is not limited to, insulin receptor, members of the insulin-like growth factor receptor family, epidermal growth factor receptor family, fibroblast growth factor receptor family, hepatocyte growth factor receptor family, vascular endothelial growth factor receptor family, neurotrophin receptor (trk) famiy, the T-cell receptor, the B cell receptor and members of the Type I–IV cytokine receptor families (Heldin, 1995, Cell. 80: 213–223; Taniguchi, 1995, Science, 268: 251–255). Adapter molecules that are substrates may include the Grb proteins, IRS-1, Zap-70 and Shc (Pawson et al., 1995, Nature 373: 573–580). Cytoskeletal proteins such as actin and transcription factors such as the STAT proteins (Ihle et al., Trends Biochem Sci, 19:222–227) may also serve as substrates. As used herein, the term ligand is synonymous with extracellular signaling molecules, and includes but is not limited to growth factors such as insulin, EGF, PDGF, fibroblast growth factors, vascular endothelial growth factor, and neurotrophins; and cytokines such as growth hormone, erythropoietin, tumor necrosis factor, interleukins and interferons. The term ligand is not limited to soluble molecules, and includes; for example, extracellular matrix proteins, cell adhesion molecules as well as antigenic peptides associated with the major histocompatibility complex proteins on the surface of an antigen-presenting cell.

In one embodiment of the invention, the compounds of the invention can be used to trigger or upregulate signal transduction in cells so that the effect of ligand binding to a receptor is enhanced, or mimicked if the ligand is not present. The compounds exert the effect by inhibiting or diminishing the activity of a phosphatase in the signaling pathway which normally acts negatively toward signaling. One mechanism by which PTPs normally downregulate signal transduction involves the dephosphorylation of specific phosphotyrosine residues (pTyr) on PTKs and their substrates since many PTKs require phosphorylation of some of its own tyrosine residues in order to become optimally active in the signaling pathway. The compounds of the invention can be used to prevent the dephosphorylation of pTyr residues on receptors or their subunits which normally becomes phosphorylated upon ligand binding, thereby enhancing the extent and duration of PTK phosphorylation. The compounds of the invention can also be used to prevent the dephosphorylation of PTKs in which the tyrosine residues become autophosphorylated or transphosphorylated due to its basal activity. In these PTKs, a signal may be triggered by the compounds of the invention in the absence of ligand binding since the basal activity of PTKs is sufficient to promote a signal if constitutive PTP activity is inhibited or diminished by the compounds.

A preferred embodiment of the invention is directed to a method of triggering, enhancing or sustaining insulin receptor signal transduction by inhibiting the constitutive dephosphorylation of the pTyr sites on the activated insulin receptor. This would allow the insulin receptor to remain phosphorylated, thus enhancing or sustaining the insulin signal. Furthermore, since it has been shown that insulin receptor is phosphorylated at a low level even in the absence of insulin (Goldstein, 1992, J. Cell Biol., 48:33–42), the compounds of the invention can be used to trigger a signal, even in the absence of insulin, by allowing the tyrosine residues on the receptor to become self-phosphorylated.

Another mechanism by which PTPs may exert a negative effect on signaling is through the dephosphorylation of specific pTyr sites to which SH2-containing molecules bind during signaling. The absence of such pTyr sites would prevent the recruitment of SH2-containing molecules to specific subcellular compartments to form multiprotein signaling complexes, thereby, preventing the further propagation of the signal. Thus, the compounds of the invention can be used to upregulate or prolong signal transduction by preventing the dephosphorylation of pTyr sites on substrate proteins that normally serve as binding sites for SH2-containing proteins which promote signaling. In another embodiment of the invention, the compounds of the invention may be used to prevent the dephosphorylation of specific pTyr residues on any substrate, which pTyr residues are essential to the transmissions or propagation of the signal. Furthermore, the compounds of the invention may be used to prevent the dephosphorylation of specific pTyr residues on any substrate, which pTyr residues are inhibitory to signal transduction.

The compounds of the invention can also be used to suppress or downregulate signal transduction in cells so that the effect of ligand binding to a receptor is abolished or attenuated. The compounds can inhibit a phosphatase in a signaling pathway which normally acts positively toward signaling. For example, PTPs promote signaling through the activation of members of the Src family of PTKs. Src family PTKs have an inhibitory site of phosphorylation in their carboxy termini which by dephosphorylation activates the kinase activity. Thus the compounds of the invention can be used to prevent the dephosphorylation of the inhibitory pTyr in the carboxy termini of kinases which function normally to promote signal transductions. Src family PTKs may include Src, Fyn, Lck, Lyn, Blk, Hck, Fgr and Yrk. Other kinases which may be similarly regulated by a phosphatase may include Fak and Csk (Taniguchi, 1995, Science 268: 251–255).

The abilities of the compounds of the invention to inhibit protein tyrosine phosphatase activity and to trigger or upregulate a cellular process which is controlled by signal transduction are demonstrated in the working example infra.

5.1. Assays for Determining the Inhibitory Activity of the Compounds

Various procedures known in the art may be used for identifying, evaluating or assaying the inhibition of activity of protein tyrosine phosphatases by the compounds of the invention. In general, such assays involve exposing target cells in culture to the compounds and a) biochemically analyzing cell lysates to assess the level and/or identity of tyrosine phosphorylated proteins; or (b) scoring phenotypic or functional changes in treated cells as compared to control cells that were not exposed to the test substance.

Where mimics of the natural ligand for a signal transducing receptor are to be identified or evaluated, the cells are exposed to the compound of the invention and compared to positive controls which are exposed only to the natural ligand, and to negative controls which were not exposed to either the compound or the natural ligand. For receptors that are known to be phosphorylated at a basal level in the absence of the natural ligand, such as the insulin receptor, the assay may be carried out in the absence of the ligand. Where inhibitors or enhancers of ligand-induced signal transduction are to be identified or evaluated, the cells are exposed to the compound of the invention in the presence of the natural ligand and compared to controls which are not exposed to the compound of the invention.

The assays described hereinbelow may be used as a primary screen to evaluate the phosphatase inhibition activity of the compounds of the invention. The assays may also be used to assess the relative potency of a compound by testing a range of concentrations, in a range from 100 μM to 1 pM, for example, and computing the concentration at which the amount of phosphorylation or signal transduction is reduced or increased by 50% (IC50) compared to controls.

5.1.1. Biochemical Assays

Target cells having a substrate molecule that is phosphorylated or dephosphorylated on a tyrosine residue during signal transduction are exposed to the compounds of the invention and radiolabelled phosphate, and thereafter, lysed to release cellular contents, including the substrate of interest. The substrate may be analyzed by separating the protein components of the cell lysate using a sodium dodecyl sulphate-polyacrylamide gel electrophoresis (SDS-PAGE) technique, in either one or two dimensions, and detecting the presence of phosphorylated proteins by exposing to X-ray film. In a similar technique, without using radioactive labelling, the protein components separated by SDS-PAGE are transferred to a nitrocellulose membranes the presence of pTyr is detected using an antiphosphotyrosine (anti-pTyr) antibody. Alternatively, it is preferred that the substrate of interest be first isolated by incubating the cell lysate with a substrate-specific anchoring antibody bound to a solid support, and thereafter, washing away non-bound cellular components, and assessing the presence or absence of pTyr on the solid support by an anti-pTyr antibody. This preferred method can readily be performed in a microtiter plate format by an automated robotic system, allowing for testing of large numbers of samples within a reasonably short time frame. The anti-pTyr antibody can be detected by labelling it with a radioactive substance which facilitates its detection by autoradiography. Alternatively, the anti-pTyr antibody can be conjugated with an enzyme, such as horseradish peroxidase, and detected by subsequent addition of a calorimetric substrate for the enzyme. A further alternative involves detecting the anti-pTyr antibody by reacting with a second antibody which recognizes the anti-pTyr antibody, this second antibody being labelled with either a radioactive substance or an enzyme as previously described. Any other methods for the detection of an antibody known in the art may be used.

The above methods may also be used in a cell-free system wherein cell lysate containing the signal-transducing substrate molecule and phosphatase is mixed with a compound of the invention and a kinase. The substrate is phosphorylated by initiating the kinase reaction by the addition of adenosine triphosphate (ATP). To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of pTyr. The results are compared to those obtained with reaction mixtures to which the compound is not added. The cell-free system does not require the natural ligand or knowledge of its identity. For example, Posner et al. (U.S. Pat. No. 5,155,031) describes the use of insulin receptor as a substrate and rat adipocytes as target cells to demonstrate the ability of pervanadate to inhibit PTP activity. As another example, Burke et al. (1994, Biochem Biophys Res Comm 204:129–134) describes the use of autophosphorylated insulin receptor and recombinant PTP1B in assessing the inhibitory activity of a phosphotyrosyl mimetic.

In addition to measuring phosphorylation or dephosphorylation of substrate proteins, activation or modulation of second messenger production, changes in cellular ion levels, association, dissociation or translocation of signaling molecules, gene induction or transcription or translation of specific genes may also be monitored. These biochemical assays may be performed using conventional techniques developed for these purposes.

5.1.2. Biological Assays

The ability of the compounds of the invention to modulate the activity of PTPs, which controls signal transduction, may also be measured by scoring for morphological or functional changes associated with ligand binding. Any qualitative or quantitative techniques known in the art may be applied for observing and measuring cellular processes which comes under the control of phosphatases in a signaling pathway. Such cellular processes may include, but are not limited to, anabolic and catabolic processes, cell proliferation, cell differentiation, cell adhesion, cell migration and cell death.

The techniques that have been used for investigating the various biological effects of vanadate as a phosphatase inhibitor may be adapted for use with the compounds of the invention. For example, vanadate has been shown to activate an insulin-sensitive facilitated transport system for glucose and glucose analogs in rat adipocytes (Dubyak et al., 1980, J Biol Chem 256:5306–5312). The activity of the compounds of the invention may be assessed by measuring the increase in the rate of transport of glucose analog, such as 2-deoxy-$^3$H-glucose, in rat adipocytes that have been exposed to the compounds. Vanadate also mimic the effect of insulin on glucose oxidation in rat adipocytes (Shechter et al., 1980, Nature 284:556–558). The compounds of the invention may be tested for stimulation of glucose oxidation by measuring the conversion of $^{14}$C-glucose to $^{14}$CO$_2$.

Moreover, the effect of sodium orthovanadate on erythropoietin-mediated cell proliferation has been measured by cell cycle analysis based on DNA content as estimated by incorporation of tritiated thymidine during DNA synthesis (Spivak et al., 1992, Exp Hematol, 20:500–504). Likewise, the activity of the compounds of the invention toward phosphatases that play a role in cell proliferation may be assessed by cell cycle analysis.

The activity of the compounds of the invention can also be assessed in animals using experimental models of disorders caused by or related to dysfunctional signal transduction. For example, the activity of the compounds may be tested for its effect on insulin receptor signal transduction in non-obese diabetic mice (Lund et al., 1990, Nature 345:727–729), BB Wistar rats and streptozotocin-induced diabetic rats (Solomon et al., 1989, Am J Med Sci 297:372–376). The activity of the compounds may also be assessed in animal carcinogenesis experiments since phosphatases can play an important role in dysfunctional signal transduction leading to cellular transformation. For example, okadaic acid, a phosphatase inhibitor, has been shown to promote tumor formation on mouse skin (Suganuma et al., 1988, Proc Natl Acad Sci 85:1768–1771).

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

The above-described assays are exemplary and not intended to limit the scope of the invention. Those of skill in the art would appreciate that modifications can be made to the assays to develop equivalent assays that obtain the same result.

5.2. The Phosphatase Inhibitors

The present invention relates to organic molecules capable of modulating and/or regulating signal transduction, in particular, by inhibiting the activity of protein tyrosine phosphatase. These compounds will be referred to herein generically as "phosphatase inhibitors", even though the compounds either upregulate or downregulate cellular processes that are controlled by signal transduction. Generally, the compounds of the instant invention are compounds described by the formula (I):

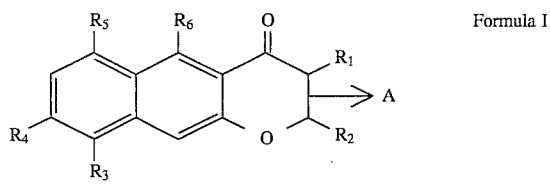

Formula I or a pharmaceutically acceptable salt thereof, wherein:
  A is a single or double bond;
  R1, R2, which are the same or different, H, are C1 to C4 substituted or unsubstituted alkyl group, or a substituted or unsubstituted aryl group;
  R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;
  R3 is a substituent identical to that of formula I providing a compound of formula II:

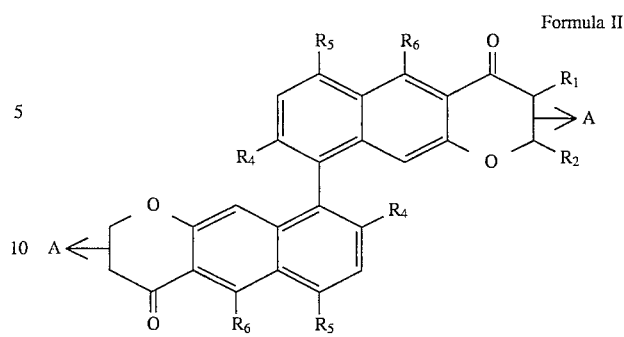

or a pharmaceutically acceptable salt thereof; or R3 is an aryl group, e.g., mono, bi or tricyclic aryl group, which may be substituted or unsubstituted; which links to formula I directly or by amide, carbon or ketone groups. Specific examples of comopunds within the scope of the invention are described infra.

5.1.3. Analogues and/or Salts

As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In addition to the above compounds and their pharmaceutically acceptable salts, the invention is further directed, where applicable, to solvated as well as unsolvated forms of the compounds (e.g., hydrated forms) having the ability to regulate and/or modulate phosphatase activity.

The compounds described above may be prepared by any process known to be applicable to the preparation of chemically-related compounds. Suitable processes are illustrated by the representative examples provided, infra. Necessary starting materials may be obtained by standard procedures of organic chemistry.

5.2. Pharmaceutical Formulations and Routes of Administration

The identified compounds can be administered to a human patient, by itself, or in pharmaceutical compositions where it is mixed with suitable carriers or excipient(s) at doses to treat or ameliorate a variety of disorders, including solid cell tumor growth, including Kaposi's sarcoma, glioblastoma, and melanoma and ovarian, lung, mammary, prostate, pancreatic, colon and epidermoid carcinoma, diabetes, diabetic retinopathy, hemangioma and rheumatoid arthritis. A therapeutically effective dose further refers to that amount of the compound sufficient to result in amelioration of symptoms of uncontrolled vasculogenesis and angiogenesis. Techniques for formulation and administration of the compounds of the instant application may be found in "Remington's Pharmaceutical Sciences," Mack Publishing Co., Easton, Pa., latest edition.

The formulations of the present invention normally will consist of at least one compound of formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, syrup B.P., methyl cellulose, polyoxyethylene sorbitan monolaurate, ethyl lactate and propylhydroxybenzoate, sorbitan trioleate, sorbitan sesquioleate and oleyl alcohol.

5.2.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. Dosage forms include but are not limited to tablets, troches, dispersions, suspensions, suppositories, solutions, capsules, creams, patches, minipumps and the like.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

5.2.2. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In addition to the common dosage forms set out above, the compounds of the present invention may also be administered by controlled release means and/or delivery devices including Alzet® osmotic pumps which are available from Alza Corporation. Suitable delivery devices are described in U.S. Pat. Nos. 3,845,770; 3,916,899; 3,536,809; 3,598,123; 3,944,064 and 4,008,719, the disclosures of which are incorporated in their entirety by reference herein.

Many of the phosphatase modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

5.2.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p1).

Dosage amount and interval may be adjusted individually to provide plasma levels of the active moiety which are sufficient to maintain the phosphatase modulating effects, or minimal effective concentration (MEC). The MEC will vary for each compound but can be estimated from in vitro data; e.g., the concentration necessary to achieve a 50–90% inhibition of the phosphatase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

Usual patient dosages for systemic administration range from 1 to 2000 mg/day, commonly from 1 to 250 mg/day, and typically from 10 to 150 mg/day. Stated in terms of patient body weight, usual dosages range from 0.02 to 25 mg/kg/day, commonly from 0.02 to 3 mg/kg/day, typically from 0.2 to 1.5 mg/kg/day. Stated in terms of patient body surface areas, usual dosages range from 0.5 to 1200 mg/m$^2$/day, commonly from 0.5 to 150 mg/m$^2$/day, typically from 5 to 100 mg/m$^2$/day. Usual average plasma levels should be maintained within 50 to 5000 μg/ml, commonly 50 to 1000 μg/ml, and typically 100 to 500 μg/ml.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Desirable blood levels may be maintained by a continuous infusion of the compound as ascertained by plasma levels measured by HPLC. It should be noted that the attending physician would know how to and when to terminate, interrupt or adjust therapy to lower dosage due to toxicity, or bone marrow, liver or kidney dysfunctions. Conversely, the attending physician would also know to adjust treatment to higher levels if the clinical response is not adequate (precluding toxicity).

The magnitude of a prophylactic or therapeutic dose of the compound in the acute or chronic management of disease will vary with the severity of the condition to be treated and the route of administration. Again, it should be noted that the clinician or physician would know when to interrupt and/or adjust the treatment dose due to toxicity or bone marrow, liver or kidney dysfunctions. The dose, and perhaps the dosage frequency, will also vary according to the age, body weight, and response of the individual patient. In general, as discussed above, the total daily dose ranges for the compounds for the majority of the disorders described herein, is from about 0.02 to about 25 mg/kg patient. Preferably, a daily dose range should be between about 0.02 to about 3 mg/kg, while most preferably a daily dose range should be between about 0.2 to about 1.5 mg/kg per day. It is further recommended that infants, children, and patients over 65 years, and those with impaired renal, or hepatic function, initially receive low doses, and that they be titrated based on individual clinical response(s) and blood level(s). It may be necessary to use dosages outside these ranges in some cases as will be apparent to those of ordinary skill in the art.

5.2.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a tumor, such as a glioma or glioblastoma and inhibition of angiogenesis.

5.3. Methods of Treatment

Any compound of the invention which inhibits or diminishes the PTP activity in a signaling pathway may be used in the therapeutic methods of the invention. In a preferred embodiment, the activity of the compound is sufficiently specific for the PTPs in the pathway so that the compound does not interfere with the function of other phosphatases in the cell. The compounds of the invention may be identified and evaluated by, for example, methods described infra.

The compounds and pharmaceutical compositions of the invention can be used for treating diabetes mellitus. The pathogenesis of diabetes generally involves insufficient or a total lack of insulin signal transduction. The paucity or absence of the insulin signal may be caused by a variety of reasons such as a lack of insulin, loss of binding affinity, defective receptor or underexpression of receptor. Insulin receptor activity can be modulated by inhibiting the phosphatases in the signaling using the compounds of the invention. Unlike currently available treatment modalities that are based on the insulin receptor, the insulin signal may be restored or stimulated in cells through the inhibition of dephosphorylating activity, even in the absence of insulin. The example of diabetes mellitus illustrates the principles of therapeutic applications of the invention which may be applied to other disorders that implicate signal transduction by phosphotyrosine phosphatases.

The compounds and pharmaceutical compositions of the invention may be used to treat immune disorders in which cytokine signal transduction is deficient. Cytokines plays a crucial role in hemopoiesis as well as coordinating immune and inflammatory responses. The compounds may be used to replace or enhance the activity of a cytokine in signaling the differentiation and proliferation of hemopoietic cells, as well as B and T cells in response to antigenic stimulation, and thus be useful for treating anemia and immunodeficiency. The compounds may also be used as an anti-inflammatory agent to treat disorders such as rheumatoid arthritis. The compounds may also be therapeutically useful in treating neurodegenerative diseases by stimulating the growth and differentiation of neuronal cells which is regulated by neurotrophin-mediated signal transduction.

In another embodiment of the invention, the compounds and pharmaceutical compositions of the invention may be used to treat cancer, such as glioma, melanoma, Kaposi's sarcoma, hemangioma and ovarian, breast, lung, pancreatic, liver, prostate, colon and epidermoid cancer, in which the malignant cells proliferate and/or metastasize as a result of uncontrolled signal transduction mediated by growth factors. For example, overexpression of a PTK, such as HER2 has been shown to correlate with the aberrant growth characteristics of tumor cells. Vasculogenesis and/or angiogenesis that facilitates tumor growth may also be inhibited by the compounds. The compounds may modulate signal transduction in these tumor cells so that normal growth characterisitics are restored. The compounds may also be useful in treating psoriasis which is caused by excessive epidermal growth factor mediated signal transduction.

Having now generally described the invention, the same will be more readily understood through reference to the following examples which are provided by way of illustration, and are not intended to be limiting of the present invention.

6. EXAMPLE: COMPOUND SYNTHESIS OR ISOLATION

The compounds of the present invention can be synthesized in accordance with standard organic chemistry techniques using readily available starting materials. Alternatively, certain compounds can be isolated as described in the working examples below. Chemical synthesis and isolation methods are provided herein for illustration. Variations of these methods may be apparent to those skilled in the art.

6.1. Example 1: 2-Methyl-5,6,8-trihydroxy-9-(5,6,8-trihydroxy-2-methyl-4H-naphtho[2,3,b]]pyran-4-one-9-yl)4H-naphtho[2,3,b]pyran-4-one (Compound 1)

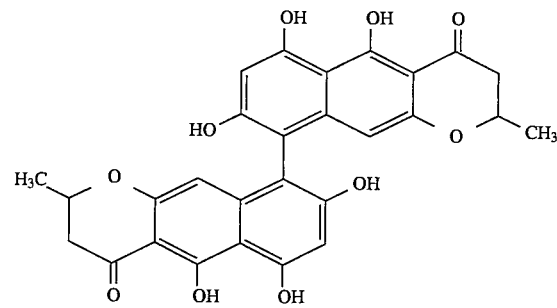

A mixture of 500 mg of 2-methyl-5,6,8-trihydroxy-4H-naphto[2,3,b]pyran-4-one and 200 mg of ferric chloride in 10 ml of dimethylformamide was heated at 95° C. for 5 hours. Addition of 20 ml of water yielded a solid after filtration. Further purification of this material on a silica gel column produced 120 mg of the title compound. 2-Methyl-5,6,8-trihydroxy-4H-naphtho[2,3,b]pyran-4-one was prepared from 3,6,8-trimethoxy-1-naphthol (CAS 94332-80-6) (Tanaka et al., Argic Biol. Chem. 27, 1963 p48–53; Bycroft, R., J. Chem. Soc., 1963 p4868–4871). A solution of 2.5 grams of 3,6,8-trimethoxy-1-naphthyl in 10 ml of toluene and 3 ml of diketene was refluxed for 5 hours. Evaporation followed by crystallization of the solid in ethyl acetate and hexane yielded 2.2 grams of 1-acetoacetoxy-3,6,8-trimethoxynaphthene. This material underwent Fries rearrangement in refluxing xylenes for 20 hours or with aluminum trichloride or boron trifluoride etherate in dichloromethane at room temperature to provide 1.8 gram of 2-acetoaceto-3,6,8-trimethoxynaphthalene. Treatment of 2-acetoaceto-3,6,8-trimethoxynaphthalene with boron tribromide in dichloromethane followed by hydrogenation of 2-methyl-5,6,8-trihydroxy-naphtho[2,3,b]pyran-4-one yielded 2-methyl-5,6,8-trihydroxy-4H-naphtho[2,3,b]pyran-4-one. Alternatively, the same sequence could be run with acroyl chloride to yield 2-methyl-5,6,8-trihydroxy-4H-naphtho[2,3,b]pyran-4-one without hydrogenation.

6.2. Example 2: 5,6-Dihydroxy-9-(5,6-dihydroxy-8-methoxy-2-methyl-4H-naphtho[2,3,b]pyran-4-one-9-yl)-8-methoxy-2-methyl-4H-naphtho[2,3,b]pyran-4-one (Compound 2)

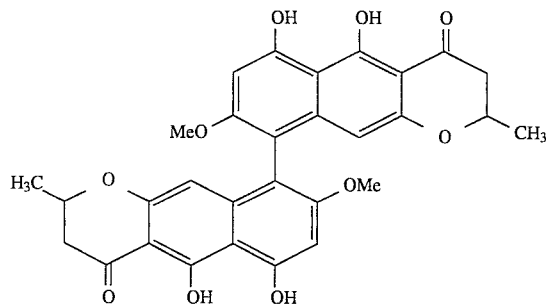

A mixture of 50 mg of 2-methyl-5,6,8-trihydroxy-9-(5,6,8-trihydroxy-2-methyl-4H-naphtho [2,3,b]pyran-4-one-9yl)-4H-naphtho[2,3,b]pyran-4-one, 100 mg of methyl iodide and 100 mg of powdered potassium carbonate was heated at 60° C. for 12 hours. The mixture was partitioned between chloroform and water. The chloroform layer was then washed with brine, dried over sodium sulfate, filtered and concentrated. The resulting solid was purified by HPLC on a C-18 silical gel column to provide 5,6-dihydroxy-9-(5,6-dihydroxy-8-methoxy-2-methyl-4H-naphtho[2,3,b]pyran-4-one-9-yl)-8-methoxy-2-methyl-4H-naphtho[2,3,b]pyran-4-one.

6.3. Example 3: 5,6-Dihydroxy-9-(6,8-dimethoxy-5-hydroxy-2-methyl-4H-naphtho[2,3,b]pyran-4-one-9-yl)-8-methoxy-2-methyl-4H-naphtho[2,3,b]pyran-4-one (Compound 3)

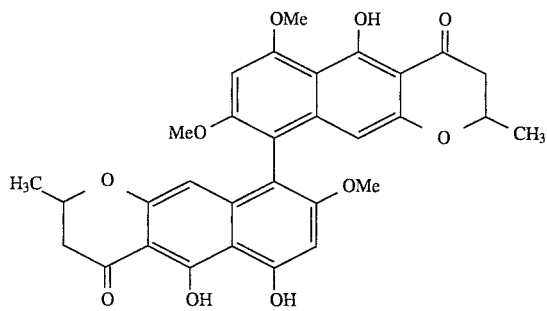

The title compound was obtained as one of the products in Example 2.

6.4. Example 4: 6,8-Dimethoxy-9-(6,8-dimethoxy-5-hydroxy-2-methyl-4H-naphtho[2,3,b]pyran-4-one-9-yl)-5-hydroxy-2-methyl-4H-naphtho[2,3,b]pyran-4-one (Compound 4)

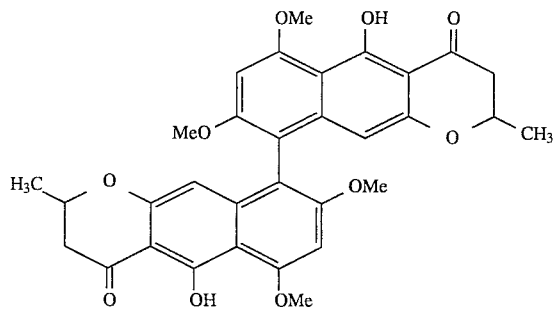

The title compound was obtained as one of the products in Example 2.

6.5. Example 5: 5,6-Dihydroxy-8-dimethylaminocarbonyloxy-9-(5,6-dihydroxy-8-dimethylaminocarbonyloxy-2-methyl-4H-naphtho[2,3,b]pyran-4-one-9-yl)-2-methyl-4H-naphtho[2,3,b]pyran-4-one (Compound 5)

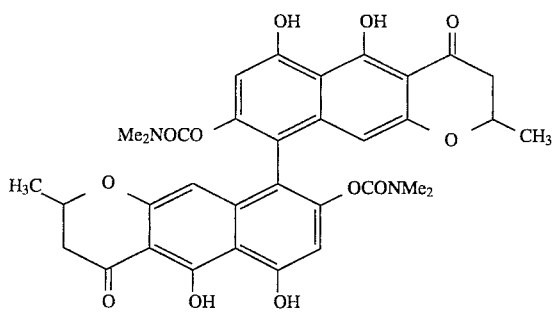

A mixture of 50 mg of 2-methyl-5,6,8-trihydroxy-9-(5,6,8-trihydroxy-2-methyl-4H-naphtho[2,3,b]pyran-4-one-9yl)-4H-naphtho[2,3,b]pyran-4-one in 2 ml of pyridine at 0° C. was added with 0.02 ml of dimethylcarbamoyl chloride. The mixture was then stirred at 0° C. for 2 hours and warmed to room temperature overnight. The mixture was quenched with 1 ml of 0.1N sodium hydroxide solution, stirred for 20 minutes and partitioned between chloroform and water. The chloroform layer was then washed with diluted hydrochloric acid solution, saturated sodium bicarbonate solution, brine, dried over sodium sulfate, filtered and concentrated. The resulting solid was purified on HPLC on a C-18 silical gel column to provide the title compound.

6.6. Example 6: 2-Methyl-5,6,8-trihydroxy-9-(5,6,8-trihydroxy-2-methyl-naphtho[2,3,b]pyran-4-one-9-yl)naphtho[2,3,b]pyran-4-one (Compound 6)

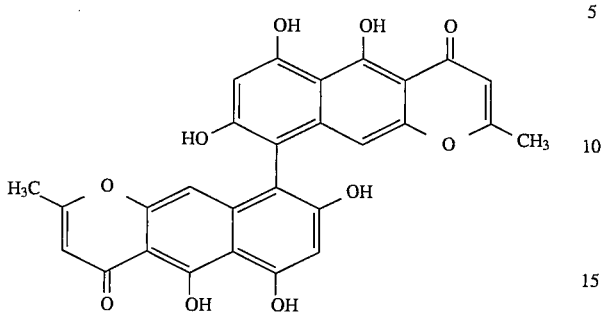

Following similar oxidative dimerization as described for Example 1 using 2-methyl-5,6,8-trihydroxynaphtho[2,3,b]pyran-4-one as the starting material (see Example 1) produced the title compound.

Similarly, Example 7 to Example 10 are prepared from Example 6 under conditions as described for Example 2 to 5.

6.7. Example 7: 5,6-Dihydroxy-9-(5,6-dihydroxy-8-methoxy-2-methylnaphtho-[2,3,b]pyran-4-one-9-yl)-8-methoxy-2-methylnaphtho[2,3,b]pyran-4-one (Compound 7)

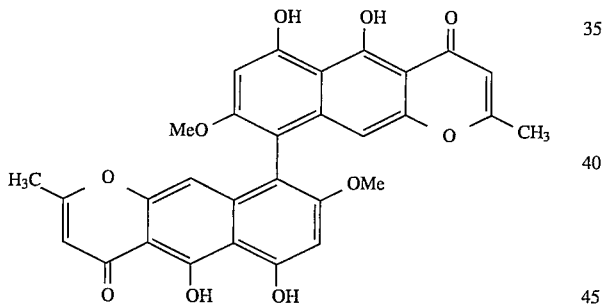

6.8. Example 8: 5,6-Dihydroxy-9-(6,8-dimethoxy-5-hydroxy-2-methyl-naptho[2,3,b]pyran-4-one-9-yl)-8-methoxy-2-methylnaphtho-[2,3,b,]pyran-4-one (Compound 8)

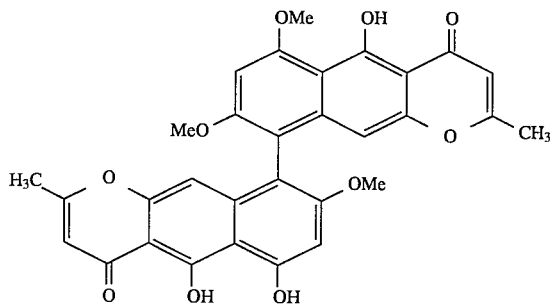

6.9. Example 9: 6,8-Dimethoxy-9-(6,8-dimethoxy-5-hydroxy-2-methylnaphtho[2,3,b]pyran-4-one-9-yl)-5-hydroxy-2-methylnaphtho-[2,3,b]pyran-4-one (Compound 9)

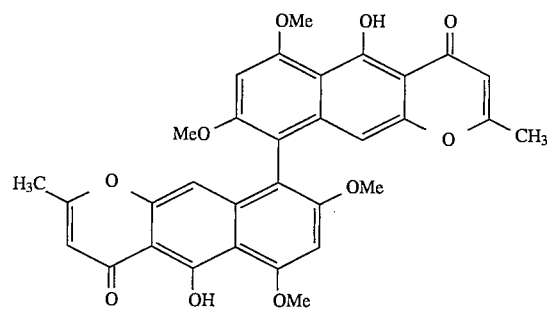

6.10. Example 10: 5,6-Dihydroxy-8-dimethylaminocarbonyloxy-9-(5,6-dihydroxy-8-dimethylaminocarbonyloxy-2-methylnaphtho[2,3,b]pyran-4-one-9-yl)-2-methylnaphtho[2,3,b]pyran-4-one (Compound 10)

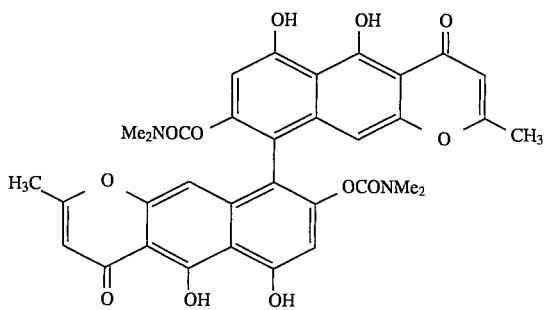

6.11. Example 11: 5,6-Dihydroxy-9-(5,6-dihydroxy-2-methyl-4H-naphtho[2,3,b]pyran-4-one-9-yl)4H-naphtho[2,3,b]pyran-4-one (Compound 11)

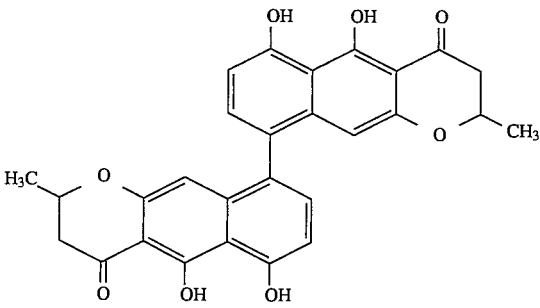

A sample of 20 mg of the crude 8,8'-dimethylsulfonate of Example 1 prepared under the similar conditions as described for Example 5 in 5 ml of ethanol with a drop of acetic acid was stirred with 20 mg of 10% palladium on carbon under 1 arm of hydrogen for 2 days. Filtration of the crude through a pad of celite followed by concentration produced the crude produced which was further purified by HPLC on a C-18 silica gel column to provide the title compound.

6.12. Example 12: 9-(3,7-Dihydroxynaphathalene-2-carbonyl)-2-methyl-5,6,8-trihydroxy-4H-naphtho[2,3,b]pyran-4-one (Compound 12)

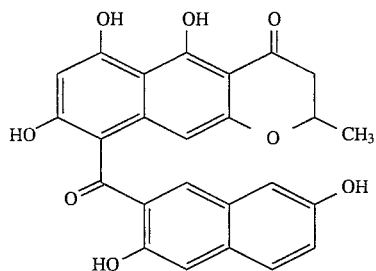

A solution of 50 mg of 2-methyl-5,6,8-trimethoxy-4H-naphtho[2,3,b]pyran-4-one in 3 ml of dichloromethane was added to a mixture of 50 mg of 3,7-dimethoxynaphalene-2-carboxyl chloride and 20 mg of aluminum trichloride in 3 ml of dichloromethane at 0° C. The mixture was stirred at 0° C. for 2 hours and warmed to room temperature overnight. The mixture was then partitioned in ethyl acetate and saturated sodium bicarbonate solution. The ethyl acetate layer was washed with brine, dired over sodium sulfate, filtered and concentrated. The crude was purified on a silica gel column twice with a solvent mixture of dichloromethane and methanol to provide 15 mg of 2-methyl-9-(3,7-dimethoxynaphathalene-2-carbonyl)-5,6,8-trimethoxy-4H-naphtho[2,3,b]pyran-4-one which was treated with excess boron tribromide in dichloromethane followed by HPLC purification of the crude on a C-18 column to provide the title compound.

6.13. Example 13: 9-(4-Hydroxyphenylaminocarbonyl)-2-methyl-5,6,8-trihydroxy-4H-naphtho[2,3,b]pyran-4-one (Compound 13)

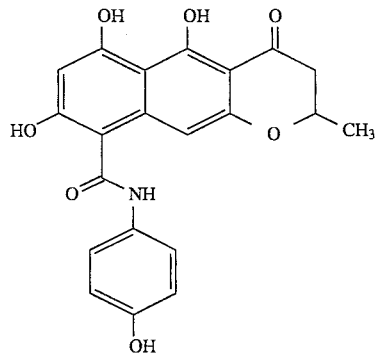

A solution of 50 mg of 9-bromo-2-methyl-5,6,8-trimethoxy-4H-naphtho[2,3,b]pyran-4-one (prepared from bromination of 2-methyl-5,6,8-trimethoxy-4H-naphtho[2,3,b]pyran-4-one in carbon tetrachloride in 30% yield) was stirred with tetrakistriphenylphosphine palladium, triethylamine in wet methanol under 20 atm of carbon monoxide for 10 hours to provide, after filtration and extraction, 9-hydroxycarbonyl-2-methyl-5,6,8-trimethoxy-4H-naphtho[2,3,b]pyran-4-one. With standard amidation conditions using mixed anhydride such isobutylchloroformate, 9-hydroxycarbonyl-2-methyl-5,6,8-trimethoxy-4H-naphtho[2,3,b]pyran-4-one was coupled with 4-hydroxyaniline followed by standard demethylation with boron tribromide to provide the title compound.

Similarly, under the conditions as described in Example 12, the compounds of Examples 14 and 15 are prepared.

6.14. Example 14: 2-Methyl-9-(4-trifluoromethylphenylaminocarbonyl)-5,6,8-trihydroxy-4H-naphtho[2,3,b]pyran-4-one (Compound 14)

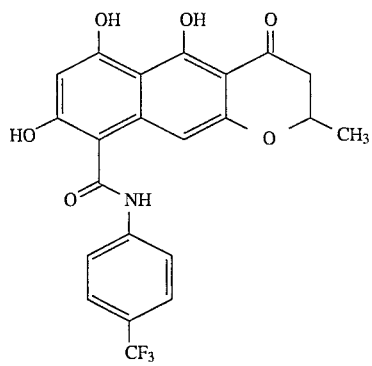

6.15. Example 15: 9-(4-t-Butylphenylaminocarbonyl)-2-methyl-5,6,8-trihydroxy-4H-naphtho[2,3,b]pyran-4-one (Compound 15)

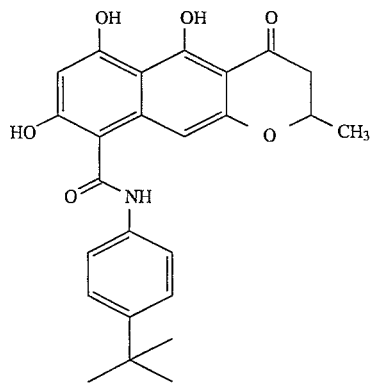

6.16. Example 16: Isolation of 2-methyl-5,6,8-trihydroxy-9-(5,6,8-trihydroxy-2-methyl-4H-naphtho[2,3,b]pyran-4-one-yl)4H-naphtho[2,3,b]pyran-4-one (Compound 1)

The present example employed a fungus culture (Penlabs Inc. #2346), and the following fermentation conditions: medium-yeast malt extract plus trace elements at 22° C. The seed medium consisted of mannitol 60.0 g; soybean meal 12.5 g, citric acid 2.5 g, yeast extract 0.5 g, $H_2O$ to 1 liter. The pH of the seed medium was adjusted to 7.0 before autoclaving. 30 ml seed medium were dispensed per 250 ml flask, which was then inoculated with 1 ml of spore/mycelium homogenate suspension. Stock cultures were maintained frozen at −80° C. in spore storage solutions.

The fermentation mixture (mycelium and broth) was homogenized and filtered through cheesecloth by suction filtration. The filtrate was extracted three times with 0.5 v/v of ethyl acetate. The ethyl acetate layers were combined and the solvent removed by rotary evaporation. The mycelium was extracted twice with 0.4 v/v of ethyl acetate. The ethyl acetate layers were combined and the solvent removed by rotary evaporation. The oily residues both containing the title compound were combined and dried on a vacuum pump overnight.

The crude extract obtained above underwent CPC fractionation on a PC Inc. high speed countercurrent chromatograph (HSCC) containing a "tripple" coil column. A 1:3:3:3 v/v/v/v of n-hexane, ethyl acetate, methanol and water was mixed and allowed to settle overnight. The lower layer was pumped into HSCC column as the stationary phase. The upper layer was used as the mobile phase. After two hours, the lower and upper layers were switched. The HSCC run was completed after four hours. The crude metabolites eluted from 13 to 21 minutes. The active fractions were pooled and evaporated under reduced pressure to dryness.

The pooled HSCC fraction (13–21) was subjected to semi-preparative HPLC (Waters HPLC system with a Waters 996 photodioarray detector using Millenium software) fractionations using the following conditions:

Two semi-preparative $C_{18}$-cartridges (25–100 mm each, Nova Pak, 6µ); Flow rate: 10 mL/min.; 20 mg of the pooled HSCC fraction 13–21 dissolved in 50 µL of DMSO; 250 µL aliquots per injection; PDA monitored at 270 nm; linear gradient of 70% $H_2O$/30% $CH_3CN$ to 100% $CH_3CN$ over 30 minutes; isocratic at 100% $Ch_3CN$ for 6 minutes; the active material eluted from 22 to 23 minutes. The active material from 2 runs were combined and evaporated under reduced pressure to dryness to yield 14 mg of the title compound.

Mass spectra were recorded on PE Sciex LC-MS model API III (Ion Spray). Mass spectral analysis gave a molecular ion of 519 $(M+H)^+$ (molecular weight:518). $^1H$ NMR spectra were recorded in $CDCl_3$ at 300 MH on a Brucker AC-300. Chemical shifts are given in ppm relative to TMS at zero ppm using the solvent peak at 7.26 ppm ($CDCl_3$) as an internal standard. 6.52(s), 5.92(s), 4.47(m), 2.67(m) and 1.40 ppm (d,J=6.23 $H_2$). $^{13}C$ NMR spectra were recorded in $CDCl_3$ at 75 MHz on a Brucker AC-300. Chemical shifts are given in ppm relative to TMS at zero ppm using the solvent peak at 77.0 ppm ($CDCl_3$) as an internal standard. 198.4, 164.6, 161.0, 160.0, 156.4, 142.0, 105.5, 102.5, 101.9, 99.9, 99.5, 73.3, 43.2 and 20.9 ppm. Melting point: M.P.>300° C.; optical rotation: $[\alpha]_D:=+529°$ (c=0.5, dioxane).

In addition, certain compounds within the scope of the present invention can be isolated in accordance with the teachings of Hegde et al., J. Antibiotics 46(2): 207–213 (1993).

7. EXAMPLE: DEMONSTRATION OF PHOSPHATASE INHIBITION ACTIVITY OF THE COMPOUNDS

7.1. Phosphotyrosine Enzyme Linked Immunosorbent Assay

In this example, the ability of the compounds of the invention to inhibit dephosphorylation of phosphotyrosine (pTyr) residues on insulin receptor (IR) is described. The assay may be used with any compounds of the invention. Those skilled in the art will recognize that other substrate molecules, such as platelet derived growth factor receptor, may be used in the assay by using a different target cell and anchoring antibody. By using different substrate molecules in the assay, the activities of the compounds of the invention toward different protein tyrosine phosphatases may be assessed. In the case of IR, an endogenous kinase activity is active at low level even in the absence of insulin binding. Thus, no insulin is needed to stimulate phosphorylation of IR. After the exposure to a compound, cell lysates were prepared and added to microtiter plates coated with anti-insulin receptor antibody. The level of phosphorylation of the captured insulin receptor was detected using an anti-pTyr antibody and an enzyme-linked secondary antibody.

7.1.1. Materials and Methods

1. The cell line used for the IR assay was NIH3T3 (ATCC# CRL 1658) engineered to over-express the human IR (H25 cells). Growth media for these cells is DMEM (Gibco) containing 10% fetal bovine serum, 1% L-glutamine, and 20 mM Hepes.

2. The anchoring antibody used was BBE which recognizes the extracellular domain of human IR and was purified by the Enzymology Laboratories, Sugen Inc.

3. PBS (Gibco): KH2PO4 0.20 g/l, K2HPO4 2.16 g/l, KCl 0.20 g/l, NaCl 8.00 g/l, pH7.2.

4. Rabbit polyclonal antiphosphotyrosine antibody (anti-pTyr) was prepared by the Enzymology Laboratories, Sugen, Inc.

5. Goat anti-rabbit IgG POD conjugate (Tago, Burlingame, Calif., Cat. No. 6430) was used as the secondary antibody.

6. TBST buffer: 50 mM Tris-HCl, 150 mM NaCl, 0.1% Triton X-100, adjusted to pH7.2 with 10N HCl.

7. Blocking buffer: PBS plus 5% milk (Carnation instant non-fat dry milk).

8. 5× HNTG buffer: 100 mM HEPES, 750 mM NaCl, 50% glycerol, 0.5% Triton X-100, pH 7.5.

9. ABTS solution: 100 mM citric acid, 250 mM Na2HPO4, 0.5 mg/ml ABTS (2,2'-azinobis(3-ethylbenzthiazlinesulfonic acid), adjusted to pH 4.0 with 1N HCl.

10. Cell lysis buffer: HNTG containing 1 mM Na3VO4 (0.5M solution kept as a 100× stock at −80° C. in aliquots), 5 mM NaP2O7 and 5 mM EDTA prepared fresh nad keep on ice until ready for use.

11. Hydrogen peroxide: 30% solution.

7.1.2. Preparation of Assay Plates

Microtiter plates (96-well, Easy Wash ELISA plate, Corning 25805-96) were coated with the anchoring antibody at 0.5 µg per well, in 100 µl PBS for at least two hours at room temperature or overnight at 4° C. Before use, the coating buffer was replaced with 100 µl blocking buffer, and the precoated assay plate was shaken at room temperature for 30 minutes. The wells were washed 3 times with water and once with TBST buffer before adding lysate.

7.1.3. Seeding Cells

Cells were grown in 15 cm culture dish (Corning 25020-100) in DMEM media containing 10% fetal bovine serum (FBS) until 80–90% confluent. The cells were harvested with trypsin-EDTA (0.25%, 0.5 ml, Gibco), resuspended in fresh medium containing 10% FBS, 1% L-glutamine and Hepes, and transferred to round bottom 96-well tissue culture plates (Corning 25806-96) at 25,000 cells/well, 100 µl/well. The cells were incubated at 37° C. at 5% $CO_2$ for 24 hours. The media was changed by inverting the plate, and adding DMEM medium containing 0.5% FBS and Hepes. The cells were further incubated overnight at 37° C., 5% $CO_2$.

7.1.4. Assay Procedure

The assay was set up in the 96-well tissue culture plate. Before adding the compounds to the cells, media in the wells was replaced by serum free DMEM medium, 90 µl per well. Positive control wells receive 80 µl DMEM. Negative controls received 90 µl DMEM. The compounds of the invention were diluted 1:10 with DMEM and 10 μl/well of the diluted test substances were transferred to the cells in the wells to achieve a final dilution of 1:100. Positive and negative control wells received 10 μl/well of dimethyl sulphoxide (DMSO) to achieve a final concentration of 1%. Positive control wells additionally received 10 μl/well of 0.1M $Na_3VO_4$ so that the final concentration is 10 mM. The tissue culture plate was shaken for 1 minute before incubation at 37° C., 5% $CO_2$. After 90 minutes of incubation, the media was removed by inversion of the plate, and 100 μl/well of lysis buffer was added to the cells. The tissue culture plate was shaken for 5 minutes and then placed on ice for 10 minutes. The cells were homogenized by repeated aspirating and dispensing, and the lysate was transferred to the corresponding wells of a precoated assay plate.

The substrate in the cell lysates was allowed to bind to the anchoring antibody for 1 hour shaking at room temperature. The lysate was then removed, and the assay plate was washed. All ELISA plate washings were done by rinsing in water 3 times followed by one rinse with TBST. The plate was dried by tapping it on paper towels. Phosphotyrosine was detected by adding 100 μl/well anti-pTyr antiserum diluted 1:3000 with TBST to the wells and incubating for 30 minutes shaking at room temperature. The unbound excess anti-pTyr antiserum was then removed, and the assay plate was washed as desribed above. A secondary antibody diluted 1:3000 with TBST, was added to the wells, and incubated for 30 minutes shaking at room temperature. The secondary antibody was then removed, the plate washed, and fresh ABTS/$H_2O_2$ (1.2 μl 30% $H_2O_2$ to 10 ml 0.5 mg/ml 2,2'-azinobis(3-ethylbenzethiazline)sulfonic acid in 100 mM citric acid, 250 mM $Na_2HPO_4$, pH4.0) was added to start color development. The reaction was stopped after 10 minutes by adding 100 μl/well of 0.2M HCl, and incubating and shaking for 1 minute. Absorbance values at 410 nm were measured by a ELISA plate reader (Dynatec MR5000).

7.1.5. Experimental Results

The activity of the compounds are represented by the concentration of the compound which produces the indicated percentage increase in the content of phosphotyrosine over the vanadate control.

Once a compound has been shown to be active in the assay, a range of concentrations of the compound is used in kinetic experiments. The increase in the pTyr level is dependent on the dose of the compound. The kinetics of the inhibition of dephosphorylation by the compound is compared to that of vanadate.

The assay may also be used for testing compounds of the invention for their ability to inhibit the dephosphorylation of other substrate molecules, such as insulin-like growth factor 1 receptor (IGF-1R) and epidermal growth factor receptor (EGFR). When assaying the effects of the compounds on the dephosphorylation of IGF-1R, NIH3T3/IGF-1R cells expressing IGF-1R starved in serum free media were seeded in the wells of tissue culture plates at a density 20,000 cells/well. The wells of ELISA plate were coated with anti-IGF-1R antibodies. For assaying the effects on EGFR, NIH3T3/EGFR cells expressing EGFR grown in media containing 0.5% for 40 hours were seeded in the wells of 96-well tissue culture plates at a density 10,000 cells/well. The wells of ELISA plate were coated with anti-EGFR antibodies.

7.2. Glucose Transport Assay

This assay was used to assess the ability of the compounds of the invention to inhibit phosphatase activity that is involved in the signaling pathway that regulates the insulin-induced facilitated transport of glucose into adipocytes. It has been shown that incubation of isolated adipocytes with vanadate resulted in a dose-dependent increase in the rate of glucose uptake. Any compounds of the invention may be tested in this assay.

7.2.1. Materials and Methods

The cell line used for the glucose transport assay was 3T3-L1, a preadipocyte cell line (American Type Culture Collection CCL92.1) which overexpress the insulin receptor. The 3T3-L1 cells were first differentiated by treating cells under confluent growth in DMEM containing 10% fetal bovine serum (FBS) with 0.5 mM 3-isobutyl-1-methyl-xanthine, 5 μg/ml porcine insulin, 250 mM dexamethasone for 2 days. The cells were then grown in DMEM containing 10% FBS and 5 μg/ml porcine insulin for two days, after which the cells were cultured in DMEM containing only 10% FBS.

Cells for use in the assay were first grown overnight in DMEM media and 1% FBS at 37° C. at 5% $CO_2$. Two hours before use, the overnight media was replaced with serum free DMEM containing 5 mM glucose. After washing the cells twice with phosphate buffered saline (PBS), serial dilutions of the compounds of the invention diluted 1:100 into DMEM were added to the wells for a final concentration range of 0.1 μM to 500 μM. Negative control wells received DMEM only. The cells were incubated with the test compound for 1–4 hours at 37° C. at 5% $CO_2$. Fifteen minutes before the end of each time point, 2-deoxy-$^3$H-glucose was added to a final concentration of 50 μM and 0.5 μCi/ml. At the end, the compound was removed, and the wells were washed twice with PBS containing 10 mM glucose. The cells were lysed with 50 μl 0.5N NaOH, and the cell lysates were transferred to a scintillation vial and mixed with 5.2 μl of glacial acetic acid. The wells were washed each with 200 μl PBS which was transferred to the corresponding scintillation vial. $^3$H radioactivity was counted with a Beckman counter.

7.2.2. Experimental Results

The compound tested in this assay (see FIG. 1) was able to increase glucose uptake in these cells in the absence of insulin.

These data indicate that the compounds of the invention can mimic the effect of insulin in increasing the rate of glucose uptake in adipocytes in the absence of insulin.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. A method of inhibiting protein tyrosine phosphatase activity which comprises administering to a mammal an effective amount of a compound having the formula (I):

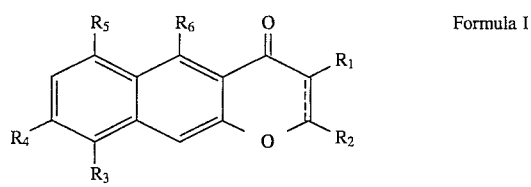

Formula I or a pharmaceutically acceptable salt thereof, wherein:

— represents a single or double bond;

R1, R2, which are the same or different, are C1 to C4 substituted or unsubstituted alkyl group or a substituted or unsubstituted aryl group;

R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;

R3 is a substituent identical to that of formula I providing a compound of formula II:

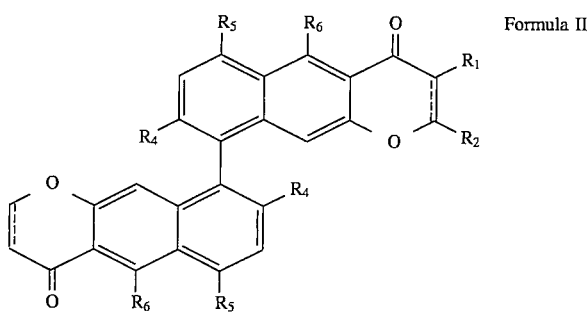

or a pharmaceutically acceptable salt thereof; or $R_3$ is a substituted or unsubstituted aryl group which links to formula I directly, or by amide, carbon or ketone groups.

2. A method of modulating signal transduction which comprises administering to a mammal an effective amount of a compound having the formula (I):

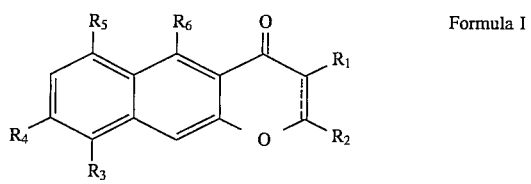

or a pharmaceutically acceptable salt thereof, wherein:

— represents a single or double bond;

R1, R2, which are the same or different, are C1 to C4 substituted or unsubstituted alkyl group or a substituted or unsubstituted aryl group;

R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;

R3 is a substituent identical to that of formula I providing a compound of formula II:

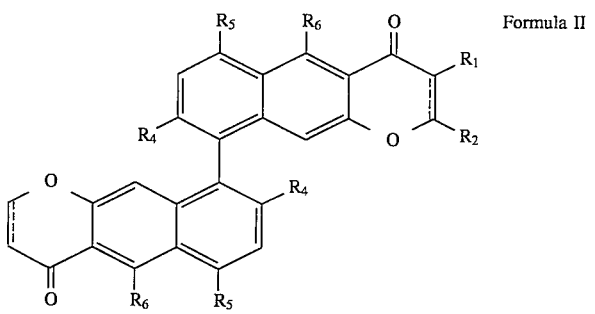

or a pharmaceutically acceptable salt thereof; or $R_3$ is a substituted or unsubstituted aryl group which links to formula I directly or by amide, carbon or ketone groups; said effective amount being sufficient to regulate protein tyrosine phosphatase activity.

3. A method of treating *Diabetes mellitus* which comprises administering to a human an effective amount of a compound having the formula (I):

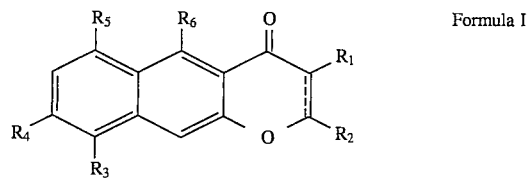

or a pharmaceutically acceptable salt thereof, wherein:

— represents a single or double bond;

R1, R2, which are the same or different, are C1 to C4 substituted or unsubstituted alkyl group or a substituted or unsubstituted aryl group;

R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;

R3 is a substituent identical to that of formula I providing a compound of formula II:

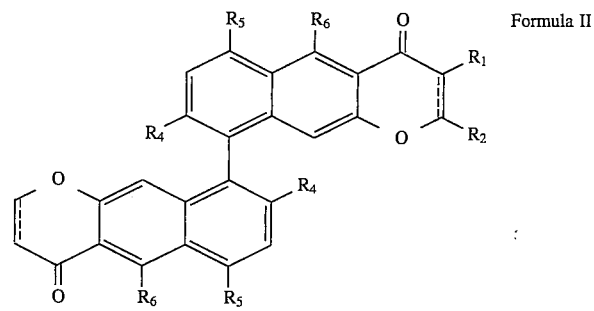

or a pharmaceutically acceptable salt thereof; or $R_3$ is a substituted or unsubstituted aryl group which links to formula I directly or by amide, carbon or ketone groups; said effective amount being sufficient to regulate protein tyrosine phosphatase activity.

4. The method of claim 1, 2 or 3 wherein said compound is

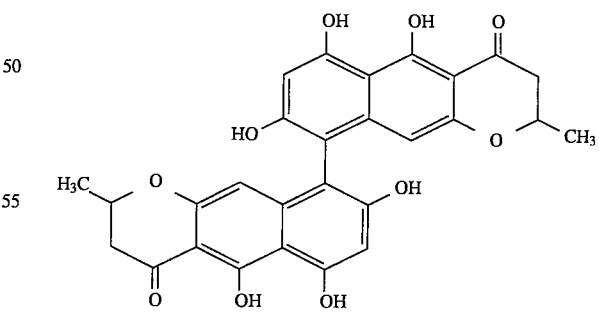

or a pharmaceutically acceptable salt thereof.

5. The method of claim 1, 2 or 3 wherein said compound is

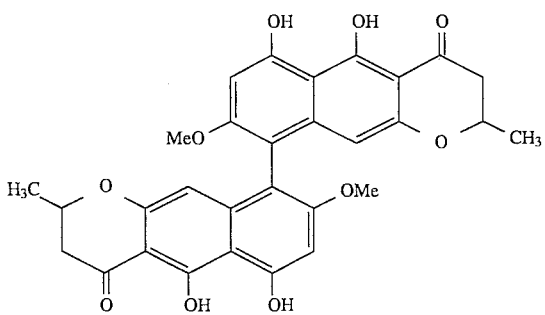

or a pharmaceutically acceptable salt thereof.

6. The method of claim 1, 2 or 3 wherein said compound is

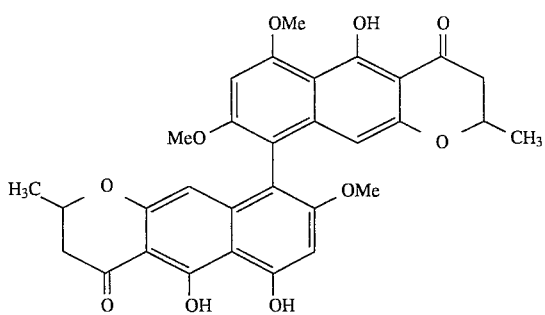

or a pharmaceutically acceptable salt thereof.

7. The method of claim 1, 2 or 3 wherein said compound is

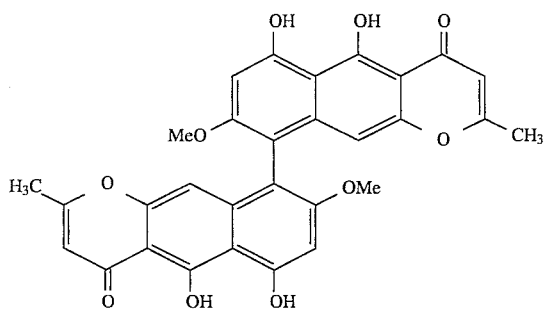

or a pharmaceutically acceptable salt thereof.

8. The method of claim 2 wherein the signal transduction is upregulated so that the effect of ligand binding to a receptor is enhanced.

9. The method of claim 2 wherein the signal transduction is upregulated so that the effect of ligand binding to a receptor is mimicked.

10. The method of claim 8 or 9 wherein the receptor is a protein tyrosine kinase.

11. The method of claim 8 or 9 wherein the receptor is insulin receptor.

12. A pharmaceutical composition which comprises an effective amount of a compound having the formula (I):

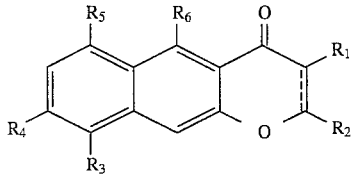

Formula I or a pharmaceutically acceptable salt thereof, wherein:
— represents a single or double bond;
R1, R2, which are the same or different, are C1 to C4 substituted or unsubstituted alkyl group or a substituted or unsubstituted aryl group;
R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;
R3 is a substituent identical to that of formula I providing a compound of formula II:

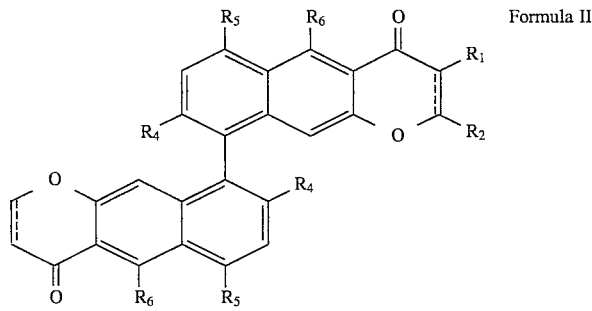

Formula II or a pharmaceutically acceptable salt thereof; or $R_3$ is a substituted or unsubstituted aryl group which links to formula I directly or by amide, carbon or ketone groups; and a pharmaceutically acceptable carrier.

* * * * *

UNITED STATES PATENT AND TRADEMARK OFFICE
CERTIFICATE OF CORRECTION

PATENT NO. : 5,602,171

DATED : Feb. 11, 1997

INVENTOR(S) : Peng C. Tang, Gerald McMahon

It is certified that error appears in the above-indentified patent and that said Letters Patent is hereby corrected as shown below:

Claims 1-3 and 12 should read as follows:

1. A method of inhibiting protein tyrosine phosphatase activity which comprises administering to a mammal an effective amount of a compound having the formula (I):

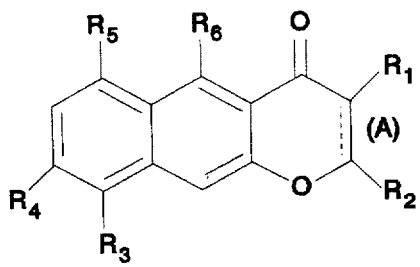

Formula I or a pharmaceutically acceptable salt thereof, wherein:
‑‑‑‑ represents a single or double bond;
$R_1$, $R_2$, which are the same or different, are C1 to C4 substituted or unsubstituted alkyl group or a substituted or unsubstituted aryl group;
$R_4$, $R_5$, $R_6$, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;
$R_3$ is a substituent identical to that of formula I providing a compound of formula II:

UNITED STATES PATENT AND TRADEMARK OFFICE
CERTIFICATE OF CORRECTION

Patent No. 6,602,171

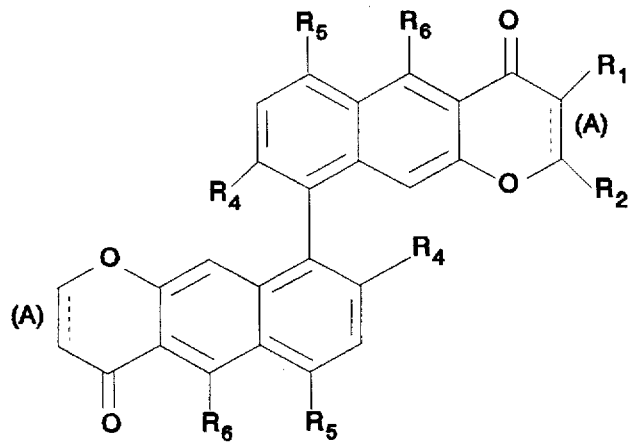

Formula II or a pharmaceutically acceptable salt thereof; or $R_3$ is a substituted or unsubstituted aryl group which links to formula I directly, or by amide, carbon or ketone groups.

2.    A method of modulating signal transduction which comprises administering to a mammal an effective amount of a compound having the formula (I):

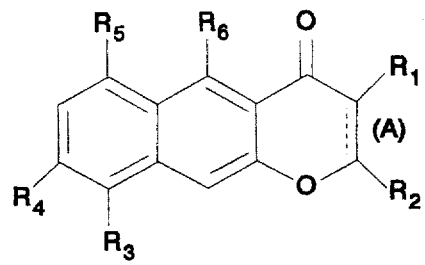

Formula I or a pharmaceutically acceptable salt thereof, wherein:
    ---- represents a single or double bond;

UNITED STATES PATENT AND TRADEMARK OFFICE
CERTIFICATE OF CORRECTION

Patent No. 5,602,171

$R_1$, $R_2$, which are the same or different, are C1 to C4 substituted or unsubstituted alkyl group or a substituted or unsubstituted aryl group;

$R_4$, $R_5$, $R_6$, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;

$R_3$ is a substituent identical to that of formula I providing a compound of formula II:

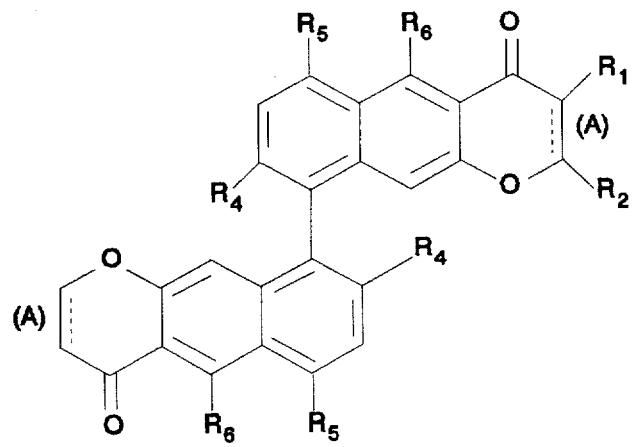

Formula II or a pharmaceutically acceptable salt thereof; or $R_3$ is a substituted or unsubstituted aryl group which links to formula I directly or by amide, carbon or ketone groups; said effective amount being sufficient to regulate protein tyrosine phosphatase activity.

3. A method of treating Diabetes mellitus which comprises administering to a human an effective amount of a compound having the formula (I):

UNITED STATES PATENT AND TRADEMARK OFFICE
CERTIFICATE OF CORRECTION

Patent No. 5,602,171

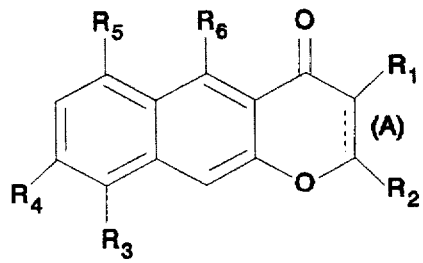

Formula I or a pharmaceutically acceptable salt thereof, wherein:
    ---- represents a single or double bond;
    $R_1$, $R_2$, which are the same or different, are C1 to C4 substituted or unsubstituted alkyl group or a substituted or unsubstituted aryl group;
    $R_4$, $R_5$, $R_6$, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;
    $R_3$ is a substituent identical to that of formula I providing a compound of formula II:

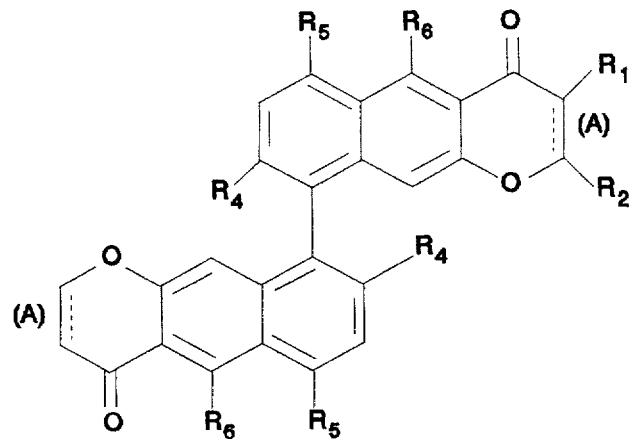

Formula II

Patent No. 5,602,171 or a pharmaceutically acceptable salt thereof; or $R_3$ is a substituted or unsubstituted aryl group which links to formula I directly or by amide, carbon or ketone groups; said effective amount being sufficient to regulate protein tyrosine phosphatase activity.

12. A pharmaceutical composition which comprises an effective amount of a compound having the formula (I):

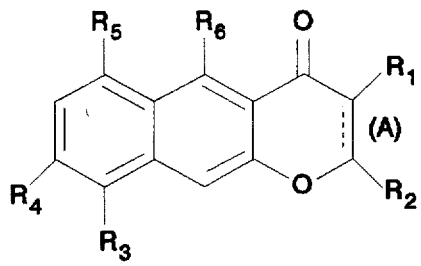

Formula I or a pharmaceutically acceptable salt thereof, wherein:
    ---- represents a single or double bond;
    R1, R2, which are the same or different, are C1 to C4 substituted or unsubstituted alkyl group or a substituted or unsubstituted aryl group;
    R4, R5, R6, which are the same or different, are H, OH, substituted or unsubstituted C1 to C4 alkoxy, substituted or unsubstituted aryl, substituted or unsubstituted C1 to C6 alkyl, alkylaryl, arylalkoxy, ester, carboxylic acid, carboxamide, carbamate, or cyano;

UNITED STATES PATENT AND TRADEMARK OFFICE
CERTIFICATE OF CORRECTION

Patent No. 5,602,171

R3 is a substituent identical to that of formula I providing a compound of formula II:

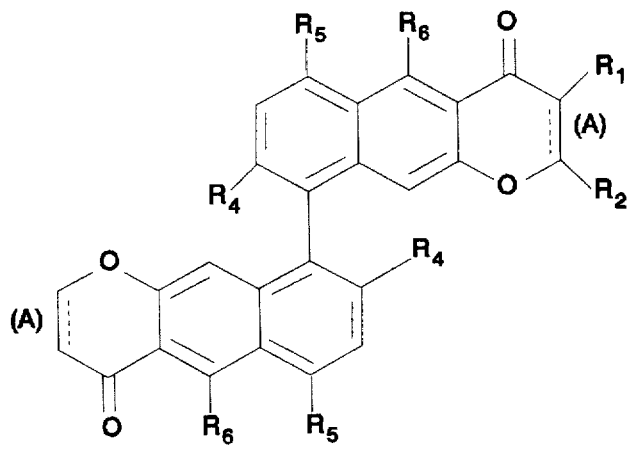

Formula II or a pharmaceutically acceptable salt thereof; or $R_3$ is a substituted or unsubstituted aryl group which links to formula I directly or by amide, carbon or ketone groups; and a pharmaceutically acceptable carrier.

Signed and Sealed this

Fifth Day of August, 1997

Attest:

BRUCE LEHMAN

Attesting Officer

Commissioner of Patents and Trademarks